United States Patent
Eidenschink et al.

(10) Patent No.: US 7,922,710 B2
(45) Date of Patent: *Apr. 12, 2011

(54) CATHETER ACCESSORY DEVICES AND METHODS OF USE

(75) Inventors: Tracee E. J. Eidenschink, Wayzata, MN (US); Richard C. Mattison, Zimmerman, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1957 days.

This patent is subject to a terminal disclaimer.

(21) Appl. No.: 10/826,786

(22) Filed: Apr. 16, 2004

(65) Prior Publication Data

US 2004/0199197 A1 Oct. 7, 2004

Related U.S. Application Data

(63) Continuation of application No. 09/862,731, filed on May 22, 2001, now Pat. No. 6,746,466.

(51) Int. Cl.
*A61M 39/02* (2006.01)

(52) U.S. Cl. ........................................... 604/539

(58) Field of Classification Search .................. 604/539, 604/165.01, 95.01, 156, 165.02; 606/194, 606/195; 600/434, 585

See application file for complete search history.

(56) References Cited

U.S. PATENT DOCUMENTS

| | | | |
|---|---|---|---|
| 4,020,829 A | 5/1977 | Wilson et al. | |
| 4,917,103 A | 4/1990 | Gambale et al. | 600/585 |
| 5,031,636 A | 7/1991 | Gambale et al. | 600/585 |
| 5,047,045 A | 9/1991 | Arney et al. | 606/194 |
| 5,055,109 A | 10/1991 | Gould et al. | |
| 5,114,403 A | 5/1992 | Clarke et al. | |
| 5,156,594 A | 10/1992 | Keith | 604/103.09 |
| 5,312,338 A | 5/1994 | Nelson et al. | |
| 5,388,579 A | 2/1995 | Dowd et al. | |
| 5,392,778 A | 2/1995 | Horzewski | |
| 5,551,443 A | 9/1996 | Sepetka et al. | |
| 5,706,827 A | 1/1998 | Ehr et al. | |
| 5,830,157 A | 11/1998 | Foote | 600/585 |
| 5,836,306 A | 11/1998 | Duane et al. | 600/585 |
| 5,851,189 A | 12/1998 | Forber | |
| 5,897,584 A | 4/1999 | Herman | |
| 5,978,699 A | 11/1999 | Fehse et al. | 600/434 |
| 6,033,414 A | 3/2000 | Tockman et al. | |
| 6,074,368 A | 6/2000 | Wright | |
| 6,096,009 A * | 8/2000 | Windheuser et al. | 604/165.01 |
| 6,190,333 B1 | 2/2001 | Valencia | 600/585 |
| 6,371,940 B1 | 4/2002 | Valencia et al. | |
| 6,440,161 B1 | 8/2002 | Madrid et al. | 623/1.11 |

(Continued)

FOREIGN PATENT DOCUMENTS

| | | |
|---|---|---|
| DE | 41 15 007 A1 | 11/1992 |
| DE | 199 48 409 C1 | 4/2001 |
| EP | 0 335 581 A2 | 10/1989 |
| WO | 99/44535 | 9/1999 |

(Continued)

*Primary Examiner* — Nicholas D Lucchesi
*Assistant Examiner* — Brooke M Matney
(74) *Attorney, Agent, or Firm* — Seager, Tufte & Wickhem, LLC

(57) ABSTRACT

A wire station is disclosed for securing and managing multiple wire members used in a catheter system. The wire management system includes means for securing the proximal portion of two wire members in a spatially separate arrangement. The wire station of the present invention additionally provides a physician with the flexibility of either directly attaching the wire station of the present invention to the catheter system directly, or positioning the wire station at a remote location.

20 Claims, 6 Drawing Sheets

U.S. PATENT DOCUMENTS

| | | | |
|---|---|---|---|
| 6,497,670 B1 | 12/2002 | Parodi | 600/585 |
| 6,551,273 B1 | 4/2003 | Olson et al. | |
| 6,682,536 B2 | 1/2004 | Vardi et al. | 606/108 |
| 6,682,556 B1 | 1/2004 | Ischinger | 623/1.35 |
| 6,689,157 B2 | 2/2004 | Madrid et al. | 623/1.11 |
| 6,796,976 B1 * | 9/2004 | Chin et al. | 604/523 |

FOREIGN PATENT DOCUMENTS

| | | |
|---|---|---|
| WO | 99/44539 | 9/1999 |
| WO | WO 99/59664 A1 | 11/1999 |
| WO | 00/13613 | 3/2000 |
| WO | WO 01/43809 | 6/2001 |

* cited by examiner

CATHETER ACCESSORY DEVICES AND METHODS OF USE

CROSS-REFERENCE TO RELATED APPLICATIONS

This application is a Continuation application of U.S. application Ser. No. 09/862,731, filed May 22, 2001, the entire content of which is hereby incorporated by reference.

TECHNICAL FIELD

The present invention generally relates to the field of intravascular medical devices and the management and operation of multiple guidewires during a medical procedure. More specifically, the present invention relates to a medical device for use in combination with a catheter system for securing and managing multiple guidewire members of a catheter system, wherein the wire station may be either directly attached to the catheter system or positioned at a remote location.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). PTCA is a well-established procedure for dilating stenosed vessel regions within a patient's vasculature. In this procedure, a balloon angioplasty catheter is introduced into the vasculature, typically through an incision in the femoral artery in the groin. The balloon catheter is then advanced through the femoral artery, through the aortic arch, and into the artery to be treated. The balloon portion of the dilation catheter is specifically advanced across the stenosis or constricted vessel, wherein the balloon is inflated. Inflation of the balloon dilates the surrounding vessel and/or displaces the plaque that forms the stenosis. The resulting treated vessel is then characterized by a greater cross-sectional area permitting additional blood flow through the previously occluded or constricted region.

It is not uncommon, however, to have these stenotic lesions form in bifurcated regions of a patient's vasculature. A bifurcation is an area of the vasculature where a first vessel is bifurcated into two or more branched vessels. Stenosis formed within a bifurcation may affect only one of the vessels, or multiple vessels comprising the bifurcated region. Treating the stenosed lesions surrounding a bifurcation can be arduous and ineffective using conventional balloon angioplasty procedures. For example, when the angle between the branch vessels in the bifurcation is small, inflation of the dilation balloon in one branch vessel can cause the ostium of the other branch vessel to collapse. The resulting angioplasty dilation procedure restricts the flow passing through the other branch vessel, thereby decreasing the effectiveness of opening the dilated vessel.

The use of vascular stents, alone or in combination with balloon dilation, is an effective alternative to conventional angioplasty procedures in bifurcated regions. Vascular stents are typically delivered to a stenosed region using a stent delivery catheter. In one common technique, the stent is crimped down into its delivery position over the inflatable balloon. The stent delivery catheter is then advanced to the lesion site under any suitable, known visualization technique. Once positioned across the stenosed lesion, the balloon of the catheter is radially expanded. The radial expansion of the balloon causes the struts of the stent to bend and to likewise expand the stent to engage the surrounding vascular wall. Once properly seated within the vessel wall, the frame of the stent opposes inward radial forces associated with vessel rebounding.

There are three basic types of intravascular catheters for use in such stent delivery procedures including fixed-wire (FW) catheters, over-the-wire (OTW) catheters and single-operator-exchange (SOE) catheters. The general construction and use of FW, OTW and SOE catheters are all well known in the art. An example of an OTW catheter may be found in commonly assigned U.S. Pat. No. 5,047,045 to Arney et al. An example of an SOE balloon catheter is disclosed in commonly assigned U.S. Pat. No. 5,156,594 to Keith.

While there have recently been considerable advances in stent design and stent deployment techniques, deployment of stents in the treatment of bifurcated lesions remains problematic, particularly where both downstream branch vessels are affected by the lesion. Current techniques of dealing with such lesions typically require the deployment of a slotted tube stent across the bifurcation. Once the first stent is deployed, the treating physician must then advance a dilation balloon between the struts of the stent already deployed in order to dilate the second branch vessel. The physician may then attempt to maneuver a second stent through the struts of the stent already deployed, into the second branch vessel for deployment. This presents significant difficulties. For example, dilating between the struts of the stent already deployed tends to distort the first stent. Numerous recent innovations in both stent designs and stent delivery catheter designs have allowed physicians to overcome these procedural difficulties.

International Application No. PCT/US99/20085 filed on Sep. 2, 1999 (hereinafter referred to as Intl. App. 99/20085), and incorporated herein by reference, discloses a system for delivering bifurcation stents. The stent deployment system includes a tubular member having a first and second end and a generally longitudinal opening between the first and second ends. The tubular member has an inner periphery sized to receive a stent therein. A plurality of apertures are disposed on opposite sides of the generally longitudinal opening. An elongate retainer is removably receivable within the apertures to retain the stent in the tubular member and to release the stent from the tubular member when removed from the apertures.

International Application No. PCT/US99/03988 filed on Feb. 24, 1999 (hereinafter referred to as Intl. App. 99/03988), and incorporated herein by reference, discloses a dilation and stent delivery system for bifurcated lesions. The stent delivery device disclosed includes a pair of dilation balloons. Each dilation balloon is coupled to a balloon catheter that is fitted within a sheath. When advanced through the tortuous vasculature of the patient, each of the dilation balloons of the stent delivery device tracks over its own guidewire, one guidewire being disposed in each branch vessel of the bifurcation.

Both of the stent delivery systems disclosed above include the use of multiple wire members in order to effect their respective stent delivery procedures. Identifying and managing numerous wire members adds unnecessary strain to a physician during a medical procedure. Due to the size, the commonality; and the shear number of wire members used, it is easy for a physician and his/her staff to be confused and delayed with the important task of wire management. Additionally, physicians painstakingly advance and withdraw these wire members within a patient's body until they are properly positioned. Once properly positioned, a physician desires to secure these wire members to insure they do not later shift. A minor shift in a wire member's placement can easily negate all of the physician's prior efforts.

SUMMARY OF THE INVENTION

The present invention overcomes many of the disadvantages of the prior art by providing a wire station that identifies, secures and manages multiple wire members of a catheter system. Additionally, the wire station of the present invention provides a physician and his/her staff with the flexibility of either directly attaching the wire station to the catheter system, or positioning the wire station at a remote location, depending upon the desired use.

The present invention discloses numerous wire management systems for identifying and securing numerous wire members. In one embodiment of the present invention, a clothespin-type wire management system is utilized on a wire station. The clothespin-type wire management station has two arm members and a coiled spring. The coil spring creates a tension that reversibly connects the two arm members together at a point distally on each arm member. At this point of contact, a common plane is formed that may grasp and retain a wire member placed therebetween.

In another embodiment of the present invention, a cullet-type wire management system is utilized on a wire station. In use, the cullet-type wire management system firmly grasps and retains a wire member that is placed between the two halves of its split center post.

In another embodiment of the present invention, a magnetic wire management system is utilized on a wire station. Magnetic regions within the magnetic wire management system possess a binding affinity to metallic wire members. This binding affinity retains a wire member that is positioned over these magnetic regions.

In yet another embodiment of the present invention, a cam-type wire management system is utilized on a wire station. Once a wire member is properly positioned within the cam-type wire management system, the circular arm of a cam is released causing the impingement of the wire member between the circular arm of the cam and a barrier wall. The impingement of the wire member is sufficient to secure the wire member positioned therebetween.

The present invention additionally provides for a wire station that can be attached to the proximal end of a catheter system. A clasping region of the wire station allows the wire station to snap over a portion of a manifold port on a catheter. Moreover, the same wire station may be removed from the proximal end of the catheter system and placed at a remote location. A weighted bag may be included with the wire station to stabilize the wire station from the release of stored torsional energy in the numerous wire members secured thereon.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Examples of construction, materials, dimensions, and manufacturing processes are provided for selected elements. All other elements employ that which is known to those skilled in the field of the invention. Those skilled in the art will recognize that many of the examples provided have suitable alternatives that may be utilized.

Figure 1A:
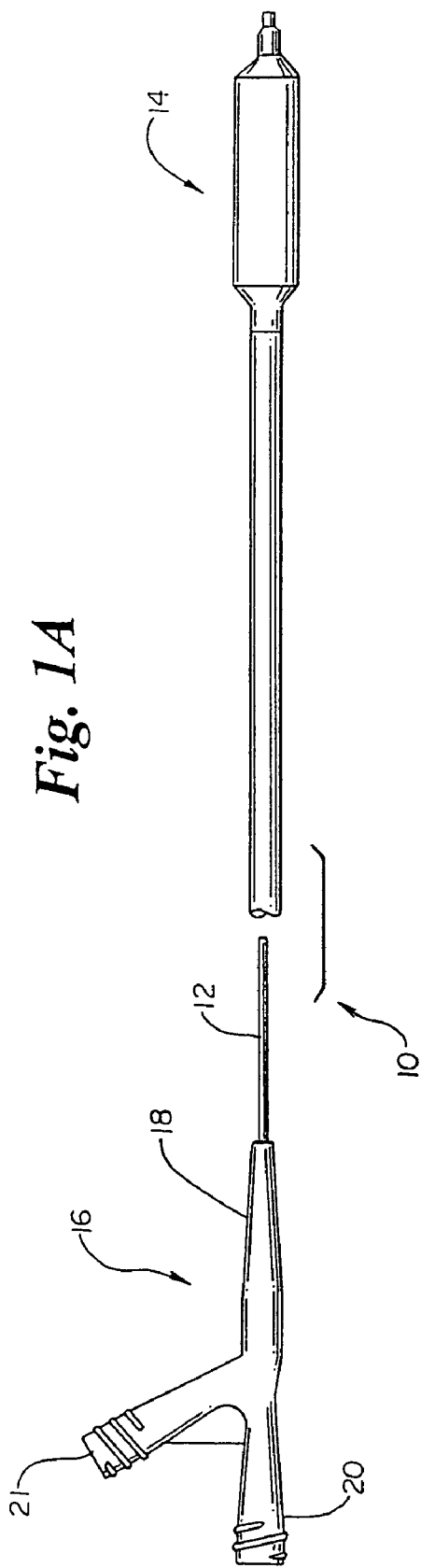
FIG. 1A is a partial perspective view of a stent delivery catheter including a single distal balloon.
Figure 1B:
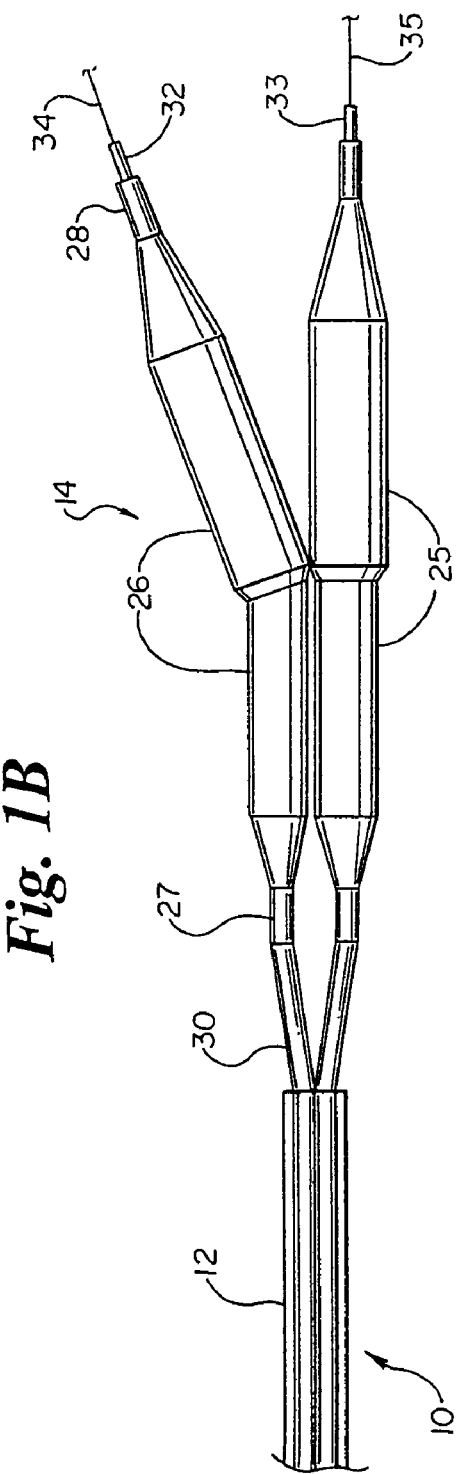
FIG. 1B is an enlarged distal view of an alternative stent delivery catheter of FIG. 1A illustrating a preferred embodiment having a dual dilation balloon assembly and multiple guidewires extending therethrough.

Referring now to the drawings, FIG. 1A is a partial perspective view of an over-the-wire (OTW) stent delivery catheter, which is representative of one type of catheter that can utilize the present invention. Other intravascular catheter embodiments are additionally suitable without deviating from the spirit and scope of the present invention. For example, intravascular catheters suitable for incorporating the present invention include fixed-wire (FW) catheters and single-operator-exchange (SOE) catheters. With respect to the structural details of the stent delivery catheter discussed below, elements common to both FIGS. 1A and 1B are numerated accordingly.

The balloon catheter 10 includes a shaft assembly 12 and a balloon assembly 14 connected proximate the distal end of shaft assembly 12. The proximal end of the shaft assembly 12 extends into a manifold assembly 16 bonded to the shaft assembly 12. Manifold ports 20 and 21 extend from the manifold assembly 16 for attaching and fluidly connecting ancillary apparatus to a lumen extending through the balloon catheter 10. As a result, each manifold port includes a lumen 22 terminating into either a common lumen or a dedicated lumen extending within the shaft assembly 12 (e.g., a guidewire lumen). The manifold ports 20 and 21 also generally include at least one male or female threaded region 24 (see FIG. 2). Referring specifically to FIG. 1A, the manifold assembly 16 comprises two luer type fitting manifold ports 20 and 21. In alternative embodiments, the union between the manifold assembly 16 and ancillary medical devices (not shown) is completed using alternative connectors. Additional attaching mechanisms between the manifold assembly 16 and ancillary medical devices, being known in the art, are also incorporated as within the scope of the present invention.

A polyurethane strain relief 18 is snap-fit to the manifold assembly 16, and the shaft assembly 12 extends into the manifold assembly 16 through the polyurethane strain relief 18.

At the distal end of the shaft assembly 12 is the balloon assembly 14. In a preferred embodiment of the present invention, specifically illustrated in FIG. 1B, the balloon assembly 14 comprises a multi-balloon design. The balloon body portion of each balloon 25 and 26 includes a proximal balloon waist 27 and a distal balloon waist 28. The proximal balloon waist 27 is connected to an outer tubular member 30 near its distal end by means of an adhesive, or alternatively, by thermal bonding. The distal balloon waist 28 is likewise connected to its corresponding inner tubular member 32 near its distal end by means of an adhesive bond or a thermal bond.

The outer tubular member 30 is co-axially disposed about the inner tubular member 32 to define an annular inflation lumen therebetween with the inner tubular member 32 extending distally from the distal end of the balloon. Because, in a preferred embodiment, two balloons 25 and 26 are individually attached to two separate inner tubular members 32 and 33, two inflation lumens are defined. It should be noted that either a dual lumen extrusion of a singular catheter shaft assembly 12 may be utilized, or in the alternative, two individual catheter assemblies may be coupled together with a sheath in order to achieve a singular catheter shaft assembly 12.

Generally, the outer tubular member 30 surrounding each inner tubular member 32 and 33 has an outer diameter ranging from 0.040 inches to 0.045 inches, with a wall thickness ranging from 0.0028 inches to 0.0044 inches. Materials used to form the outer tubular member 30 may vary depending upon the stiffness desired for the shaft assembly 12. In preferred embodiments, the outer tubular member may be made of a generally flexible polymer such as polyethylene. Marlex HDPE is a particularly suitable material for flexible outer tubular members. Using flexible polymers to form the outer tubular member often enhances catheter performance in such embodiments. For example, coupling two individual catheter assemblies together, as depicted in FIG. 1B and described in detail above, permits manufacturers to use more flexible materials for the outer tubular member. Alone, an outer tubular member having a polyethylene outer tubular member may be too flexible for proper advancement within a patient's tortuous vasculature. When two outer tubular members are coupled, however, the resultant catheter shaft possesses both the proper stiffness for advancement and the agility for vascular navigation.

It is also desirable to form the outer tubular member from a more rigid polymer to aid in catheter pushability. Nylon and similar polyamides such as DURETHAN (available from Bayer) are particularly suitable for rigid outer tubular members. Other suitable materials for a rigid outer tubular member 30 include polyetheretherketone (PEEK), polyimide (PI), and polyetherimide (PEI). Polyether block amide (PEBA), in contrast, is a relatively flexible polymeric material having a durometer of approximately 70 D. Finally, the use of a polyamide such as CRISTAMID (available from Elf Atochem) imparts a slightly less rigid durometer than the rigid polyamides and slightly greater than the flexible PEBA material. These materials are particularly suited for a single, uncoupled catheter shaft.

The inner tubular members 32 and 33 (hereinafter discussed with respect to individual inner tubular member 32) define a guidewire lumen, which each provide a passage for at least one guidewire 44,46. The inner tubular member 32 is generally made of polyethylene such as Marlex HDPE. In alternative embodiments, the inner tubular member 32 is lined with a lubricious material such as polytetrafluoroethylene (PTFE). At the proximal end of the inner tubular member 32, the inner tubular member 32 has an outside diameter ranging from 0.024 inches to 0.026 inches, and most preferably about 0.025 inches. The inner diameter of the inner tubular member 32 measures approximately 0.0167 inches to 0.0195 inches. The inner tubular member 32 has a wall thickness ranging from 0.0026 inches to 0.004 inches, and most preferably about 0.0032 inches. The outside diameter-to-wall thickness ratio must be sufficiently small to minimize the propensity for the shaft assembly 12, and more specifically the inner tubular member 32, from kinking.

As mentioned above, each dilation balloon 25 and 26 is attached at the proximal balloon waist 27 to an outer tubular member 30 and at the distal balloon waist 28 to an inner tubular member 32,33, thereby defining a dedicated inflation lumen and guidewire lumen for each balloon. These separate inflation lumens, in one embodiment, are individually connected to separate inflation sources. This embodiment permits physicians to control the inflation and deflation of each dilation balloon 26 and 27 independently. Such control is particularly useful in stent deployment procedures. In particular, such control in bifurcated lesions allows a physician to deploy a stent in one branch vessel using a first balloon 25 while maintaining the patency of a second branch vessel with the second balloon 26. This deployment procedure prevents the ostium of the second branch vessel from collapsing during the inflation of the other balloon. Additionally, utilizing two independently adjustable balloons greatly reduces the working time associated with stent deployment procedures. For example, a bifurcation stent having a single body portion, or a bifurcation stent including multiple segments, may be loaded onto a single multi-balloon catheter. Furthermore, the same loaded multi-balloon catheter may accurately deploy the bifurcation stent, and its multiple segments if applicable, at the bifurcated lesion site. This design, therefore, reduces the prior need for multiple catheters to deploy the individual segments of a typical bifurcation stent.

FIGS. 2-6 show embodiments incorporating various wire station designs for use in the management and operation of multiple guidewires emanating from the manifold assembly 16 of a catheter 10. In general, the wire station is a versatile ancillary medical device that must readily adapt to the physician's needs, as well as the circumstances and the layout of the particular medical procedure. The wire station must be easy to handle and manipulate. Wire members used in such medical procedures, including guidewires, generally have diameters in the range of 0.012 inches to 0.018 inches. A physician must be able to identify the particular wire member desired and adjust it appropriately when called upon to do so. Thus, it is desirable to manufacture a wire station that is easy for a physician to operate despite the sizes of the wire diameters being manipulated. It is additionally desirable to manufacture a mobile wire station. Often, a physician may wish to have the wire station and the contents held thereon immediately accessible. One of the most accessible locations is attached to the catheter 10 itself. At other times, the physician desires the wire station to be handy, but remote from the dynamics surrounding the procedure. In order to confidently position a wire station remotely, the wire station must be capable of maintaining its relative position with respect to the patient's body at all time. The wire station, therefore, must incorporate features that secure the wire station despite its small size and insubstantial weight.

Figure 2:
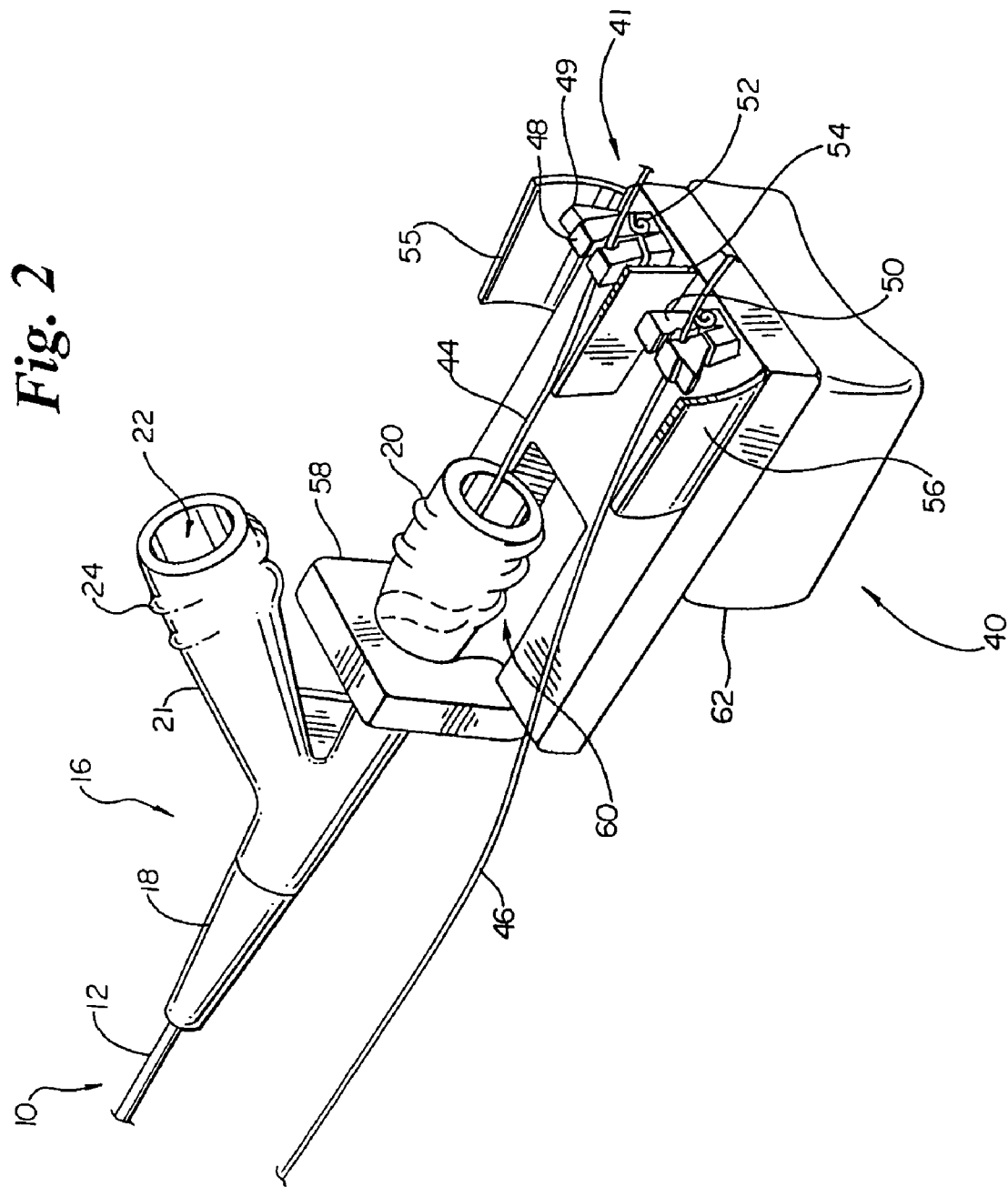
FIG. 2 is a partial perspective view of a preferred wire station attached to the proximal end of the catheter of FIG. 1, the wire station having a clothespin-type wire management system.

FIG. 2 depicts a preferred wire station 40 having a clothespin-type wire management system 41. The wire station 40 is generally comprised of a base platform 42 and a wire management system 41. The wire management system 41 both identifies its corresponding wire member 44 (extending from the manifold assembly 16) and 46 (a guidewire used with an SOE balloon catheter), as well as secures the wire member when desired. In particular to FIG. 2, the wire management system 41 functions similar to a clothespin. The clothespin-type mechanism has two arm members 48 and 50 and a coiled spring 52. The coil spring 52 creates a tension that reversibly connects the two arm members 48 and 50 together at a point distally on each arm member.

The distal end of each arm member 48,50 includes a flat portion. When flat portions of two arm members contact one another, a common plane is formed that may grasp and retain a wire member 44 placed therebetween. In one embodiment, a sponge-like material is disposed over at least a portion of the distal end of each arm member 48 and 50. Embodiments possessing such sponge-like material are characterized as having improved frictional retention of a wire member 44 when placed therebetween. In an alternative embodiment, the distal end of each arm member 48 and 50 forming the common plane possesses a series of ridges for gripping wire members 44 and 46 placed therebetween. In yet another embodiment, a semi-circle (not shown) is cut into each of the two arm members 48 and 50 near their distal ends. In this embodiment, when the two arm members 48 and 50 contact one another to form a common plane, an opening is formed within the plane. Generally, the opening formed has a diameter slightly larger than the wire member 44 desired to be retained. When the opening is slightly larger than the wire member 44, the opening permits a wire member 44 to "float" within the opening. Floating, as defined within this application, refers to the ability of the wire member 44 to move longitudinally, while otherwise being spatially restrained. A physician may find the floating of a wire member 44 particularly useful when making minor position adjustments during the advancement and retraction of wire members 44 and 46.

In the clothespin-type wire management system 41, a portion of at least one arm member 50 is secured to the base platform 42. In particular to FIG. 2, the clothespin retaining mechanisms 41 are secured so that distal ends of each arm member 48 and 50 face upwardly away from the base platform 42. When the clothespin wire management system 41 is at rest, the unattached arm member 48 of each clothespin is hinged so that their flat distal ends contact their respective attached arm member 50 to form a common plane, described in detail above.

In order to facilitate separation of the unattached arm member 48 from the attached arm member 50, a wing member 49 is affixed to the unattached arm member 48. Applying a downward pressure upon the wing member 49 of an unattached arm member 48 causes the unattached arm member 48 to pivot about the coiled spring 52. Such pivoting separates the distal end of the unattached arm member 48 from the attached arm member 50, thereby permitting a wire member 44 to be placed within or liberated therefrom.

Due to the size and unmanageability of most wire members, wire stations may be equipped with shielding devices to aid in separation and control of the wire members disposed thereon. FIG. 2 shows two such shielding devices. The first shielding device 54 physically separates the two clothespin-type wire management systems 41 from one another. This first shield 54 generally comprises a piece of polymeric or metallic material that physically attaches to the base platform 42 and extends tangentially from the base platform 42. The height of the first shield 54 may vary from wire station to wire station. In general, the height of the first shield 54 is sufficient to deflect unfastened wire members from extending over and onto the opposite side of the shield. Concurrently, the shield height should not hinder a physician from properly operating the clothespin-type wire management system 41.

The second shielding device 55 and 56 functions in a similar manner and comprises similar materials to the first shielding device 54. The primary distinction between the two shielding devices is their placement. The second shielding device 55 is positioned on the edge, or thereabout, of the base platform 42. Placing the second shielding device 55 on the edge of the base platform 42 allows the second shielding device 55 to deflect any unfastened wire members 44 that are biased to extend over the edge. In one embodiment, the second shielding device 55 may be bowed inwardly, as depicted in FIG. 2. Bowing the second shielding device 55 aids in wire member deflection, thereby maintaining all wires members within the confines of the wire station 40. By using a combination of first and second shielding devices, a wire member may easily be constrained within the confines of the clothespin-type wire management system 41. Although, these shielding devices are illustrated specifically with respect to the clothespin-type wire management system 41 of FIG. 2, these shielding devices are easily adaptable to the wire management systems of FIGS. 3-6. Illustration of the shielding devices with respect to FIG. 2 is presented by way of example and not by way of limitation. It is therefore within the scope of the invention to include shielding devices known in the art, where appropriate, on the remaining wire station embodiments.

The shape of a wire station's base platform 42 allows a physician to be flexible in the method of treatment during a patient's medical procedure. As depicted in FIG. 2, the base platform 42 is reversibly attached to the proximal end of a catheter's manifold assembly 16. In particular, the base platform 42 is attached over the non-threaded region of a manifold port 20. Attachment of a wire station 40 to the manifold assembly 16 of a catheter 10 is aided using a clasping portion 58 of the base platform 42. The clasping portion 58 of the base platform 42 extends generally tangentially from the remainder of the base platform 42. At the center of the clasping portion 58 is an opening that at its center closely mimics the outer diameter of a manifold port 20. At the base of the opening, the body of the clasping portion 58 extends inwardly, partially occluding the above-described opening from the remainder of the base platform 42. The base platform 42 further includes a second opening 60 within the main portion of the base platform 42. This second opening 60 is sized to permit the passage of a manifold port 20 therethrough.

In operation, the wire station base platform 42 is attached to the body of the manifold assembly 16 by first slipping a manifold port 20 through the second opening 60 within the main portion of the base platform 42. Because the opening within the clasping portion 58 of the base platform 42 is partially occluded, the manifold port 20 is unable to immediately slide into the clasping portion's opening. Applying a sufficient pushing pressure to the manifold port 20, however, will breach the partial occlusion leading to the clasping portion's opening. Once the partially occluded section is breached, the manifold assembly snaps into place within the confines of the opening. The once restrictive partial occlusion now holds the entire manifold port securely within the confines of the clasping portion's opening. In one embodiment, the walls of the clasping portion's opening are lined with materials that aid in the manifold port's friction fit within the opening. In particular, the walls of the opening may include a releasable pressure sensitive-adhesive material. Alternatively, the walls of the opening may include a tacky sponge-like material. The above embodiments reduce rotational movement of the wire station 40 about the connected manifold port 20. In alternative embodiments, some rotation of the wire station 40 is desired about the manifold port 20.

At times, a physician desires the close proximity of the wire station 40 to the proximal end of a catheter 10. At other times, however, it is more desirable to have the wire station 40 positioned remotely from the proximal end of the catheter 10. A weighted bag 62 attached to the bottom of the base platform 42 is particularly useful for such occasions. As shown in FIG. 2, the weighted bag 62 is attached to the distal end of the base platform 42. Placement of the weighted bag 62 at additional locations along the base platform 42 is additionally possible without deviating from the spirit and scope of the present invention.

The weighted bag 62 generally covers an area under the base platform 42 that inhibits tipping of the wire station 40 in any one direction. In one embodiment, the outer diameter of the weighted bag 62 generally traces the outline of the base platform 42. In an alternative embodiment, the outer diameter of the weighted bag 62 exceeds the outline confines of the base platform 42.

Another characteristic associated with the weighted bag 62 concerns its weight. Physicians painstakingly advance and withdraw wire members 44 and 46 inserted within a patient's body. Once properly positioned, a physician desires to secure these wire members to a wire station 40 to insure they do not later shift. A minor shift in a wire member's placement can easily negate all of the physician's efforts. One of the most common causes of incidental wire member shifting is due to torsional or rotational forces. Torsional forces are stored within a wire member during the navigation and advancement of the wire member through the patient's vasculature. The unanticipated release of these stored torsional forces in the wire member may result in a small, yet significant, shifting of the wire station 40 and wire member 44, if not properly weighted. The weighted bag 62 of the present invention prevents most movements associated with incidental displacement caused by the release of stored torsional forces within a secured wire member 44. In general, only intentional movement of wire members 44 and 46, or the wire station 40 itself, will cause the wire station 40 of the present invention having a weighted bag 62 to shift.

In order to further reduce unintentional shifting of the weighted bag 62, the weighted bag 62 may comprise a frictional material. In one preferred embodiment, the weighted bag 62 comprises a latex material. In alternative embodiments, the outside wall of the weighted bag 62 is tackified using various suitable pressure-sensitive adhesives, or the like.

Materials used within the weighted bag 62 are generally highly conformable. In preferred embodiments, the weighted bag 62 is filled with polymer beads, sand or a gel-like material. These materials transfer their own conformability to the weighted bag 62 as a whole. Conformability allows the weighted bag 62 to be placed on uneven surfaces that would otherwise compromise the stability of the attached wire station 40. For example, placing a weighted bag 62 having a rigid and straight bottom surface upon a patient's leg would result in significant instability for the wire station 40. One can easily imagine such an embodiment teetering on the patient's fleshy leg tissue. In contrast, a gel filled weighted bag 62 would easily conform and drape over the fleshy tissue. The gel filled bag readily distributes its weight around the leg tissue, resulting in greater stability for the wire station 40 as a whole. Using a conforming material within the weighted bag 62, alone or in combination with earlier-described embodiments, permits physicians to secure wire members 44 and 46 to a remote position, with confidence that they will not shift during a medical procedure.

In yet another embodiment, the weighted bag 62 may be selectively attached to the underside of the base platform 42. In this embodiment, the weighted bag 62 includes one side of a Velcro material. The matching side of the remaining Velcro material is positioned on the underside of the base platform 42. As such, the weighted bag 62 may be attached to or removed from the base platform 42 depending upon the desired need. Other means for selectively attaching the weighted bag 62 to the base platform 42 being known in the art are also incorporated as within the spirit and scope of the present invention.

Although, in relation to the catheter 10 illustrated in FIGS. 1A, 1B, and Intl. App. 99/03988, where two guidewires are managed, in alternative embodiments, such as disclosed in Intl. App. 99/20085, numerous thin wire members must be retained and identified. In the latter disclosed situation, multiple wire management systems may be added to the base platform 42 of a single wire station. Additionally, a combination of wire management systems, discussed in detail below, can be placed on the single wire station. Varying the style and placement of wire management systems allows a physician greater flexibility in managing the numerous wire members being utilized during a medical procedure. Furthermore, the ability to vary the wire management systems placed on a wire station allows the physician to customize the wire station to a particular procedure or patient. Such versatility enables a physician to easily identify and manipulate a series of similar wire members that would otherwise confuse and delay the physician during the medical procedure.

Figure 3B:
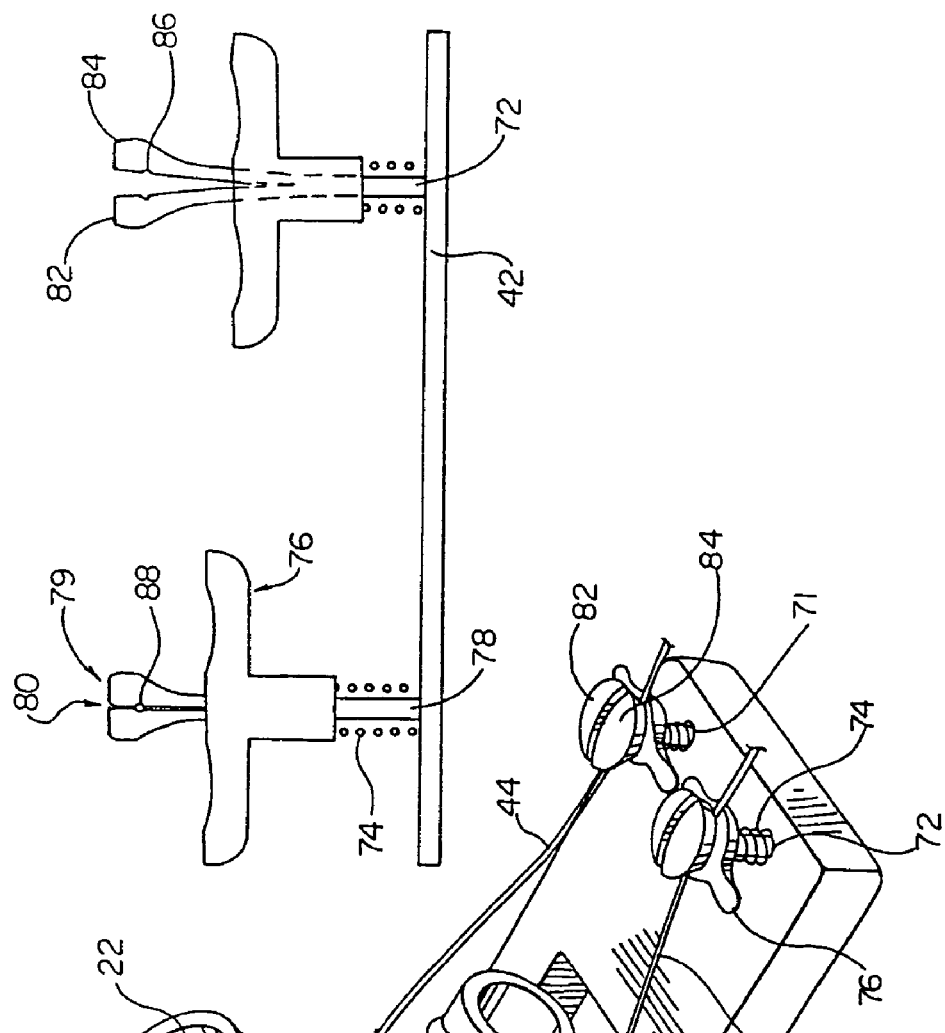
FIG. 3B is a cross-sectional view of the preferred wire station of FIG. 3A, illustrating the operation of the cullet-type wire management system.
Figure 3A:
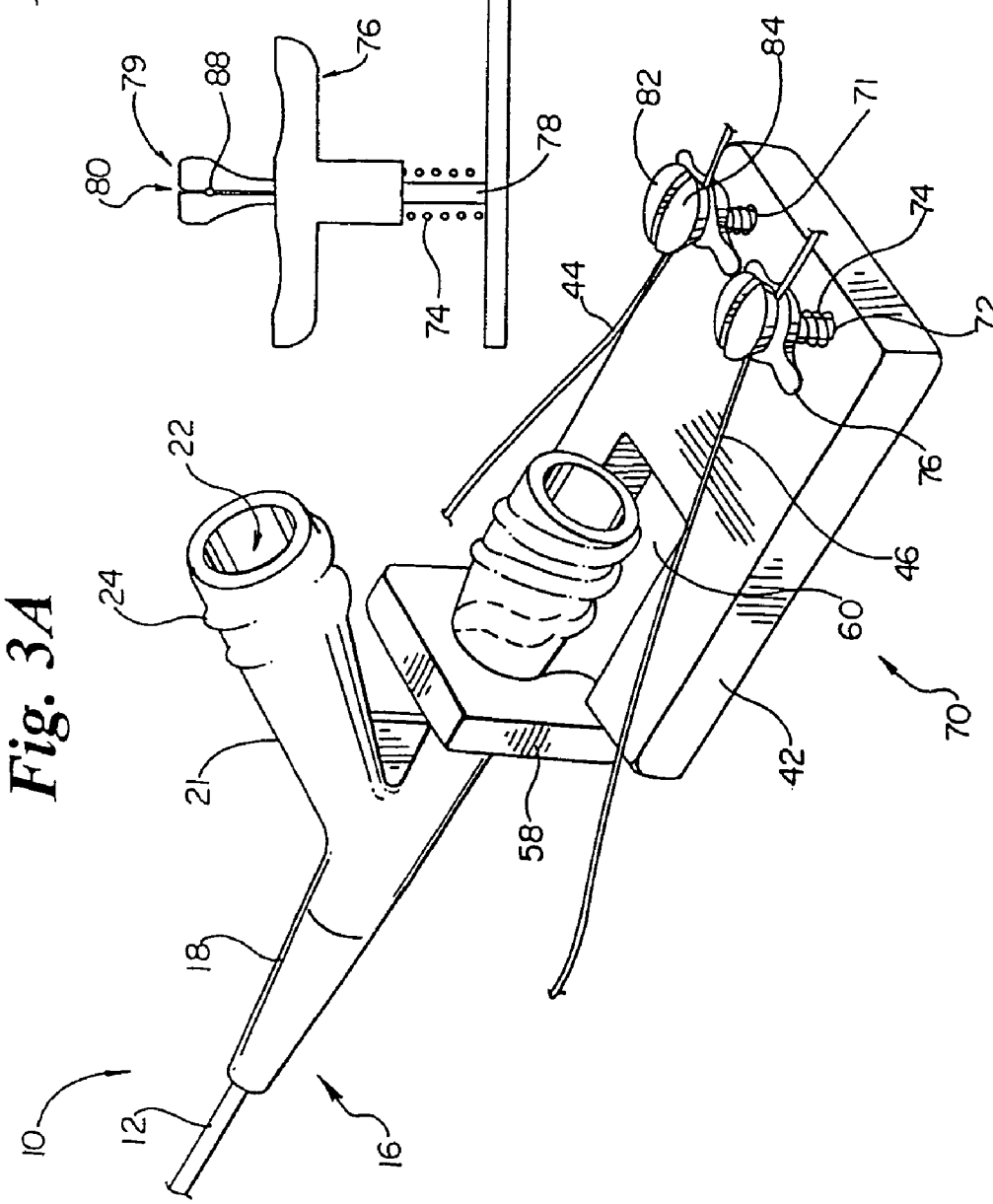
FIG. 3A is a partial perspective view of a preferred wire station attached to the proximal end of the catheter of FIG. 1, the wire station having a cullet-type wire management system.

Refer now to FIG. 3A, wherein a wire station 70 having a cullet-type wire management system 71 is shown. The wire station 70 of FIG. 3A is similar in construction to the wire station 40 described in FIG. 2. In particular, the wire station 70 depicted in FIG. 3A includes a base platform 42 with a clasping portion 58 for attaching the wire station 70 to the proximal end of a manifold assembly 16. The wire station 70 of FIG. 3A, however, does vary from that of FIG. 2 by including an alternative wire management system in lieu of the clothespin-type wire management system 41. The wire management system illustrated in both FIGS. 3A and 3B is that of the cullet-type design. With respect to the structural details of the cullet-type wire management system 71 discussed below, elements common to both FIGS. 3A and 3B are numerated accordingly, and are best comprehended when the Figures are viewed together.

The cullet-type wire management system 71 comprises three basic elements: a split center post 72, a coiled spring 74 and a push arm 76. The split center post 72 has a proximal end 78 and a distal end 79. The proximal end 78 of the split center post 72 is anchored into the base platform 42 of the wire station 70. In one embodiment, the split center post 72 is a cylindrical rod. In an alternative embodiment, the split center post 72 may be a square rod. Alternative rod shapes, being known in the art, are also incorporated as within the spirit and scope of the present invention.

As the split center post 72 extends distally from the base platform 42, the diameter of the split center post 72 increases. In a preferred embodiment, however, the split center post 72 only begins to increase in diameter at approximately half its length. The portion of the split center post 72 proximal the increased diameter portion generally maintains a uniform diameter. The split center post 72 additionally includes a single bilateral fissure 80. The fissure 80 starts distal of the proximal end on the split center post 72 and extends distally through the remainder of the post, illustrated best with reference to FIG. 3B. In a preferred embodiment, the bilateral fissure 80 terminates approximately half way through the length of the spit center post 72. The bilateral fissure 80 causes the two halves 82 and 84 of the split center post 72 to be biased outwardly when in a relaxed state. An applied pressure must be exerted to close the two halves 82 and 84 of the split center post 72 into a single generally circular form.

Positioned over the split center post 72 is a push arm 76. The push arm 76 possesses a T-shape body. Running through the length of the push arm 76 is a lumen of a continuous size. In preferred embodiments, the lumen diameter within the push arm 76 closely mimics the size of the outer diameter of the split center post 72 at its proximal-most end 78. The "arms" of the push arm element 76 extend outwardly away from the body of the element.

Surrounding the proximal-most end 78 of the split center post 72 is a coiled spring 74. The coiled spring 74 applies an expansionary force that extends along the length of the split center post 72. In particular, the coiled spring 74 applies a pressure that drives the push arm 76 distally over the split center post 72.

In operation, because the push arm 76 lumen is continuous and the split center post 72 increases in radial diameter distally, when the push arm 76 is driven distally over the split center post 72, the push arm 76 forces the two bilateral halves 82 and 84 of the split center post 72 together. Similarly, when a compression force is applied to the coiled spring 74 via the arms of the push arm 76, the coiled spring 74 compresses and the two halves 82 and 84 of the split center post 72 return to their relaxed state of separation, as depicted with arrows in FIG. 3B. When the compression force is eliminated, however, the push arm 76 is again driven distally by the coiled spring 74 causing the two halves 82 and 84 to once again be forced together. This simple mechanical operation best describes the function behind the cullet-type wire management system 71. FIG. 3A specifically illustrates wire members 44 and 46 being restrained between the two bilateral halves 82 and 84 of the split center post 72 of the cullet-type wire management system 71.

In use, the cullet-type wire management system 71 may firmly grasp and retain a wire member 44 that is placed between the two halves 82 and 84 of the split center post 72. Although the force driving the two halves 82 and 84 of the split center post 72 is sufficient to secure a wire member placed therebetween, additional modifications to the cullet-type wire management system 71 may further insure the immobilizing nature of the system. In one embodiment, a sponge-like material is disposed over at least a portion of each half 82 and 84 of the split center post 72. Embodiments possessing such sponge-like material are characterized as having improved frictional retention of a wire member when placed therebetween.

In an alternative embodiment, each half 82 and 84 of the split center post 72 possesses a series of ridges for gripping wire members 44 and 46 placed therebetween.

In yet another embodiment, a semi-circle 86 is cut into each half 82 and 84 of the split center post 72 at a point proximal the distal end 79 of the split center post 72. In this embodiment, when the two halves 82 and 84 of the split center post 72 encounter one another, an opening 88 is formed within the post. Generally, the opening 88 formed has a diameter slightly larger than the wire member 44 desired to be retained. When the opening 88 is slightly larger than the wire member 44, the opening 88 permits a wire member 44 to "float" within the opening 88. A physician may find the floating of a wire member 44 particularly useful when making minor position adjustments during the advancement and retraction of wire members.

The wire station 70 in FIG. 3A, although not illustrated as having a weighted bag disposed upon the bottom of the base platform 42, may include a weighted bag as discussed in detail above. Thus, the device can be utilized connected to the manifold or remote from the manifold. Similarly, although the wire station in FIG. 3A is not illustrated as having shielding devices to aid in separation and control of the wire members 44 and 46 disposed thereon, these devices may easily be incorporated into the final wire station design.

Figure 4:
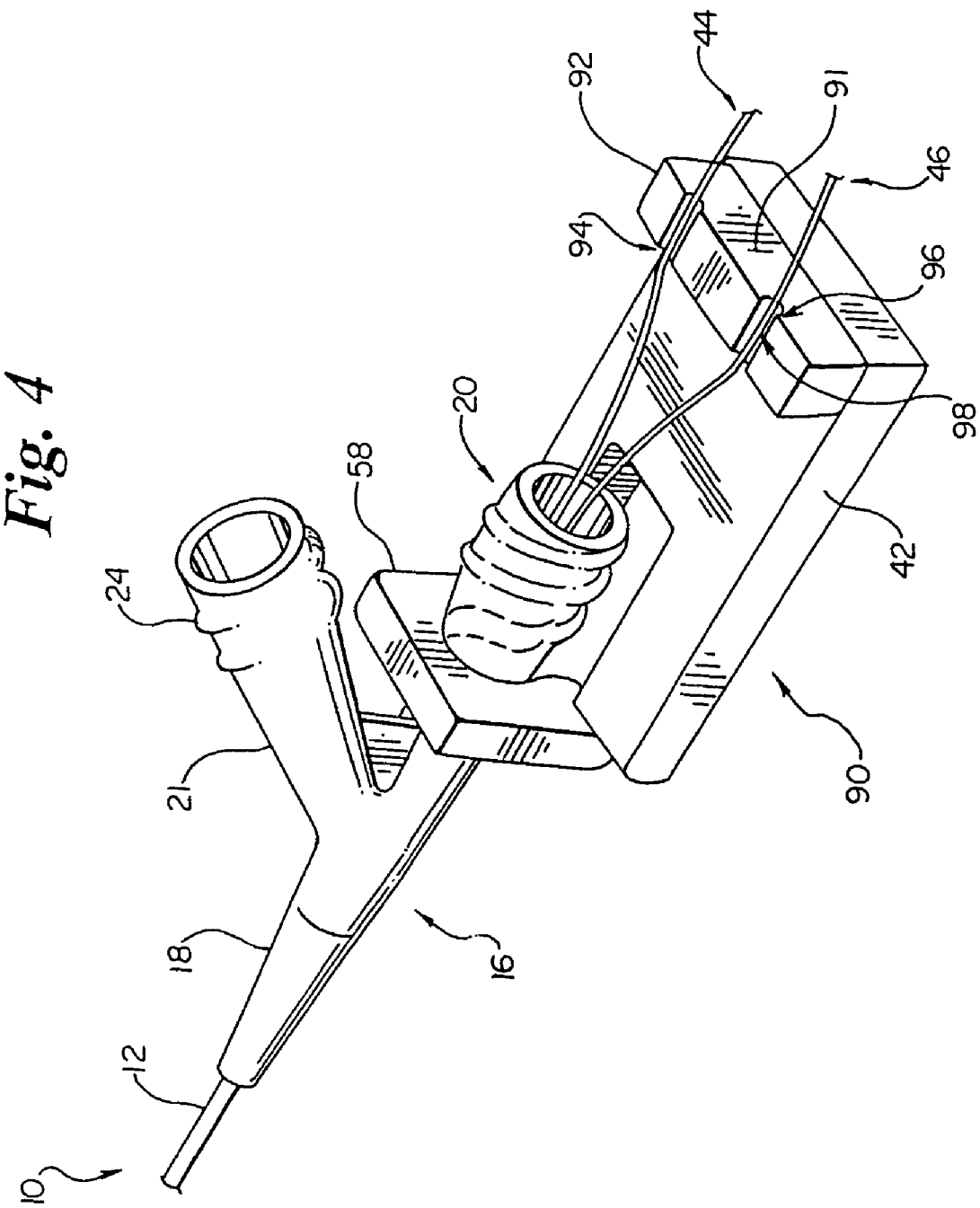
FIG. 4 is a partial perspective view of a preferred wire station attached to the proximal end of the catheter of FIG. 1, the wire station having a magnetic wire management system.

Refer now to FIG. 4, wherein a wire station 90 having a magnetic wire management system 91 is shown. The wire station 90 of FIG. 4 is similar in construction to the wire stations described in FIGS. 2 and 3A. In particular, the wire station 90 depicted in FIG. 4 includes a base platform 42 with a clasping portion 58 for attaching the wire station 90 to the proximal end of a manifold assembly 16. The wire station 90 of FIG. 4, however, does vary from those of FIGS. 2 and 3A by including an alternative wire management system in lieu of those described earlier. The wire management system illustrated in FIG. 4 is that of the magnetic design.

The magnetic wire management system 91 is positioned at the proximal end of the wire station base platform 42. In one preferred embodiment, the magnetic wire management system 91 includes an elevated body element 92. The height of the elevated body element 92 is approximately the same height as the center of the manifold port 20 lumen that the wire station 90 is attached to. It is believed that maintaining the height of the elevated body element 92 at a height equal to that of the manifold port 20 lumen provides greater ease of handling of wire members 44 and 46 being extending therefrom.

At least a portion of the elevated body element 92 is magnetic and, therefore, has a positive affinity to metallic wire members 44 and 46. In preferred embodiments, specific regions of the elevated body element 92 are magnetic, whereas other portions are not. In alternative embodiments, multiple magnetic wire management systems 91 may be added to the base platform 42 of a single wire station 90. In these embodiments, the various magnetic wire management systems 91 may be staggered on the base platform 42 or they may be separated by shielding devices (discussed in detail above).

In yet another embodiment, a combination of wire management systems, including the magnetic wire management system 91, can be placed on the single wire station. Varying the style and placement of wire management systems allows a physician greater flexibility in managing the wire members 44 and 46 being utilized during a medical procedure. Furthermore, the ability to vary the wire management systems placed on a wire station allows the physician to customize the wire station to a particular procedure or patient. Such versatility enables a physician to easily identify and manipulate a series of similar wire members that would otherwise confuse and delay the physician during the medical procedure.

The single elevated body element 92 illustrated in FIG. 4 possesses two regions 94 and 96 having magnetic properties. The magnetic regions of the magnetic wire management system of the present invention are those regions having a recessed channel 98 extending through a portion of the top planar surface of the elevated body element 92. Recessing the magnetic regions 94 and 96 within a channel 98 provides greater securing strength for wire members 44 and 46 placed therein. In contrast to a simple planar magnetic surface, a recessed channel 98 provides greater magnetic surface contact for securing metallic wire members. A recessed channel 98 further restrains wire member movement within the confines of the channel 98. As a result, accidental spatial displacement of a wire member 44 disposed within such magnetic channels 98 is limited. Moreover, recessing the magnetic regions 94 and 96 further enables a physician to easily identify those regions of the wire station having magnetic properties. A recessed channel 98 is easy to visualize and, therefore, increases the efficiency of a physician during a medical procedure. Increasing the efficiency of a physician may expedite a procedure's duration and, subsequently, reduce trauma and recovery associated with the procedure.

The wire station 90 in FIG. 4, although not illustrated as having a weighted bag disposed upon the bottom of the base platform 42, may include a weighted bag as discussed in detail above. Thus, the device can be utilized connected to the manifold or remote from the manifold. Similarly, although the wire station in FIG. 4 is not illustrated as having shielding devices to aid in separation and control of the wire members 44 and 46 disposed thereon, these devices may easily be incorporated into the final wire station design.

Figure 5:
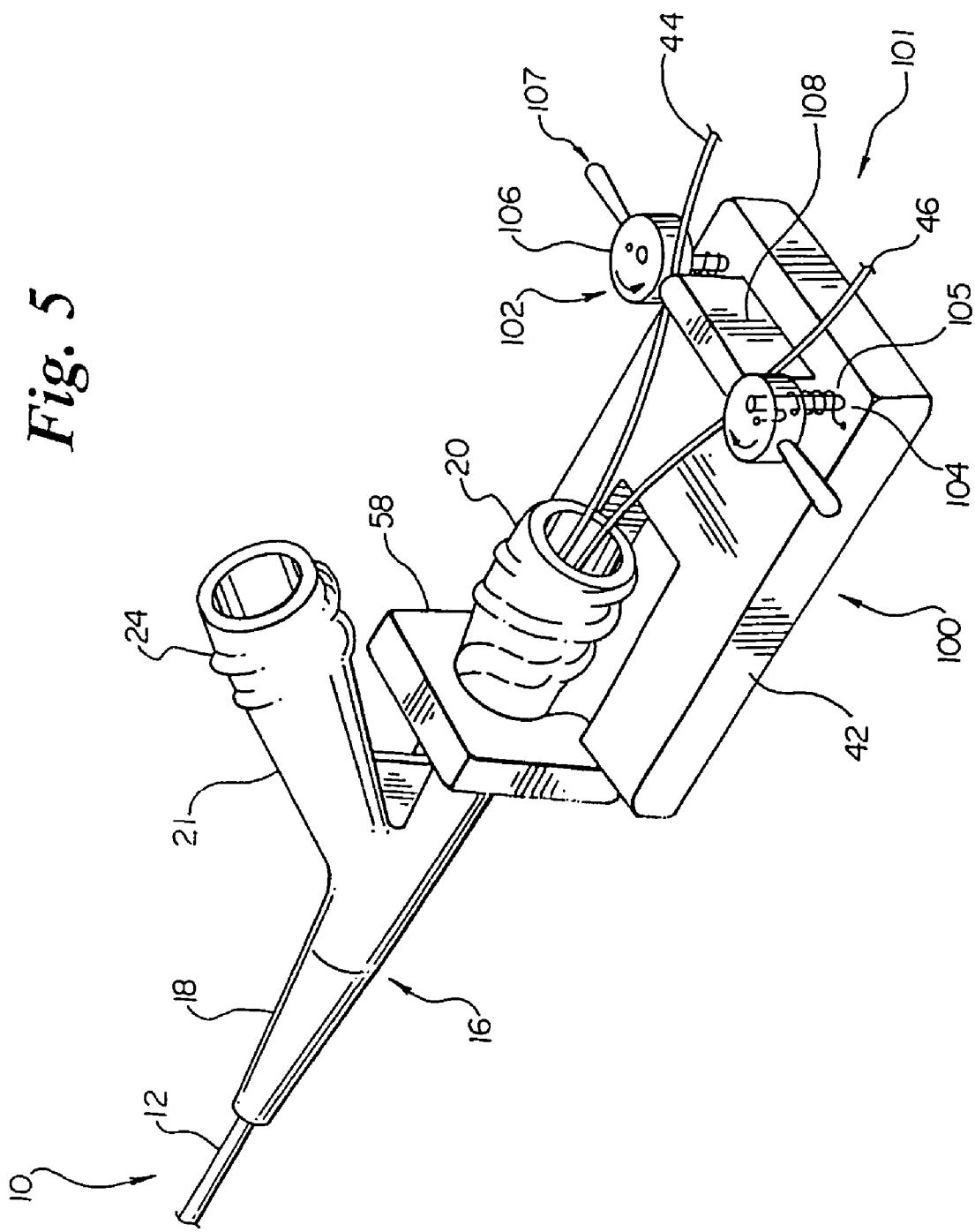
FIG. 5 is a partial perspective view of a preferred wire station attached to the proximal end of the catheter of FIG. 1, the wire station having a cam-type wire management system.

Refer now to FIG. 5, wherein a wire station 100 having a cam-type wire management system 101 is shown. The wire station 100 of FIG. 5 is similar in construction to the wire stations described in FIGS. 2, 3A and 4. In particular, the wire station 100 depicted in FIG. 5 includes a base platform 42 with a clasping portion 58 for attaching the wire station 100 to the proximal end of a manifold assembly 16. The wire station 100 of FIG. 5, however, does vary from those of FIGS. 2, 3A and 4 by including an alternative wire management system in lieu of those described earlier. The wire management system illustrated in FIG. 5 is that of the cam-type design.

The cam-type wire management system 101 restrains a wire member 44 by impinging the wire member 44 between a cam 102 and a barrier wall 108. The cam 102 of the wire management system 101 comprises three elements: a post 104, a coiled spring 105 and a circular arm 106. The post 104 of the cam 102 has a proximal end and a distal end. The proximal end of the post 104 is attached to the base platform 42 of the wire station 100. The distal end of the post 104 is attached to the circular arm 106. More specifically, the circular arm 106 is attached to the post 104 at a point slightly askew from the center of the circular arm 106. As a result, when the circular arm 106 is rotated about the post 104, the rotational movement is non-uniform. In order to facilitate the rotational movement of the circular arm 106 about the post 104, a projecting member 107 is attached to the side of the circular arm 106. Pushing or pulling on the projecting member 107 moves the circular arm 106 in either a clockwise or a counterclockwise fashion.

The coiled spring 105 circles the post 104 of the cam-type wire management system 101. The proximal and distal ends of the coiled spring 105 are attached to the base platform 42 and the circular arm 106, respectively. Tension within the coiled spring 105 forces the circular arm 106 to be biased in one rotational direction. The circular arm 106 is restrained from turning into this one rotational direction by a barrier wall 108.

The barrier wall 108 is an element that extends upwardly in a tangential direction from the body of the base platform 42. In preferred embodiments, the barrier wall 108 is formed from a frictional material. In one embodiment, the barrier wall 108 is comprised of two sections. The first section is a rigid framework that is connected to the base platform 42. The second section is a frictional pliable material that covers at least a portion of the first section. The pliable material of the first section is less resilient than the material forming the first section and, therefore, partially succumbs to pressure when so applied. In succumbing to such pressure, the pliable material conforms to the object applying the pressure. Objects abutting the second material, therefore, have greater surface contact with the frictional material forming the second section. This combination of pliability and friction causes an abutting object to be securely restrained against the barrier wall 108 as a whole. In an alternative embodiment, the circular arm 106 of the cam 102 comprises a first section and a second section similar to that described with relation to the barrier wall 108.

The barrier wall 108 abuts the circular arm 106 so that rotation in the biased direction is limited. The circular arm 106, however, can be rotated in the opposite rotational direction (against the biased direction) to displace the circular arm 106 from the barrier wall 108. When the force turning the circular arm 106 is removed, the circular arm 106 again turns in its biased direction until the rotational movement is once again restricted by the circular arm's abutment with the barrier wall 108. In operation, a physician positions a wire member 44 between the circular arm 106 and the barrier wall 108 after turning the circular arm 106 against its biased direction. Once properly positioned, the circular arm 106 is released causing the impingement of the wire member 44 between the circular arm 106 of the cam 102 and the barrier wall 108. The impingement of the wire member 44 is sufficient to secure a wire member 44 placed therebetween. Spatial displacement of the wire member 44 in a longitudinal direction can be further prevented during the impingement if the circular arm 106, the barrier wall 108, or both possess a conformable surface. FIG. 5 specifically shows wire members 44 and 46 restrained between the circular arm 106 of a cam 102 and the barrier wall 108.

Multiple cam-type wire management systems 101 may be added to the base platform 42 of a single wire station. In these embodiments, the cams 102 in the cam-type wire management systems 101 may abut their own individual barrier wall 108, or as shown in FIG. 5, share a common barrier wall 108. In yet another embodiment, a combination of wire management systems, including the cam-type wire management system 101, can be placed on the single wire station. Varying the style and placement of wire management systems allows a physician to customize the wire station to a particular procedure or patient.

The wire station 100 in FIG. 5, although not illustrated as having a weighted bag disposed upon the bottom of the base platform 42, may include a weighted bag as discussed in detail above. Thus, the device can be used as mounted on the manifold or remote from a manifold. Similarly, although the wire station in FIG. 4 is not illustrated as having shielding devices to aid in separation and control of the wire members 44 and 46 disposed thereon, these devices may easily be incorporated into the final wire station design.

Figure 6:
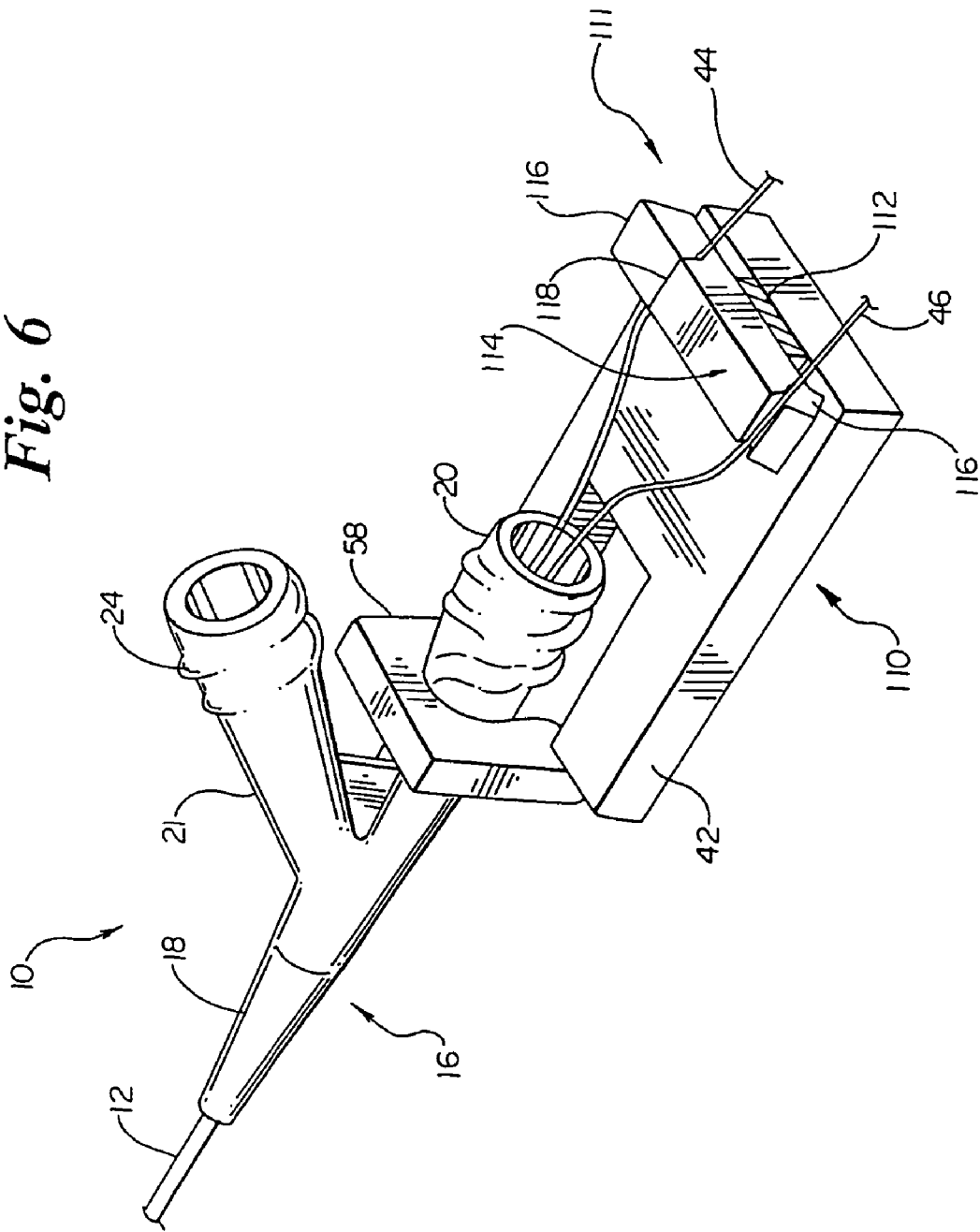
FIG. 6 is a partial perspective view of a preferred wire station attached to the proximal end of the catheter of FIG. 1, the wire station having a partial slit wire management system.

Refer now to FIG. 6, wherein a wire station 110 having a partial slit wire management system 111 is shown. The wire station 110 of FIG. 6 is similar in construction to the wire stations described in FIGS. 2, 3A, 4 and 5. In particular, the wire station 110 depicted in FIG. 6 includes a base platform 42 with a clasping portion 58 for attaching the wire station 110 to the proximal end of a manifold assembly 16. The wire station 90 of FIG. 4, however, does vary from those of FIGS. 2, 3A, 4 and 5 by including an alternative wire management system in lieu of those described earlier. The wire management system illustrated in FIG. 4 is that of the partial slit design.

The partial slit wire management system 111 is positioned at the proximal end of the wire station base platform 42. In one preferred embodiment, the partial slit wire management system 111 includes two block members—a first block member 112 and a second block member 114. In embodiments having two block members, the first block member 112 is affixed to the base platform 42. The second block member 114 is subsequently affixed upon the first block member 112, elevating the second block member 114 off the base platform 42. Generally, the second block member 114 is longer than the first block member 114. In these embodiments, the ends 116 of the second block member 114 extend over the first block member 112. In alternative embodiments, only the second block member 114 is utilized in the partial slit wire management system 111.

The second block member 114 is generally made of an elastomeric material such as nitrile rubber, butyl rubber, silicone rubber, polyurethane rubber, styrene butadiene copolymer, polystyrene foam, polychloroprene, thermoplastic polyolefin rubbers, as well as other suitable materials. These materials are both pliable and resilient. In particular, these materials may be molded into a desired shape, manipulated into a second shape, and later will return to their original molded configuration once the manipulation ceases.

The ends 116 of the second block member 114 are generally tapered so that the length of the side of the second block member 114 facing upward (hereinafter termed the "exposed face") is longer than the side that is affixed to the first block member 112. Additionally, the second block member 114 generally includes at least one partial slit 118. In preferred embodiments, the partial slits 118 are positioned near the ends 116 of the second block member 114. The partial slits 118 slice through the exposed face of the second block member 114 to a point approximately half through the second block member 114 where the slits 118 terminate. In preferred embodiments, the termination point within the body of the second block member 114 includes a circular lumen. The circular lumen has a diameter slightly larger than the wire member 44 desired to be retained. When the circular lumen is slightly larger than the wire member 44, the circular lumen permits a wire member 44 to "float" within the circular lumen. A physician may find the floating of a wire member 44 particularly useful when making minor position adjustments during the advancement and retraction of wire members.

In one embodiment, by applying a downward pressure upon an end 116 of the second block member 114, depicted by an arrow in FIG. 6, the end displaces from the remaining portion of the second block member 114 at the slit 118. Once displaced, a physician may insert a wire member 44 within the slit 118 or liberate one therefrom. Releasing pressure upon the end 116 of the second block member 114 causes the end 116 to once again retain its original shape, securely clasping any contents held within the slit 118.

In an alternative embodiment, a wire member 44 may simply be pushed through the exposed face of the second block member 114 at the partial slit 118. The wire member 44 is subsequently liberated from the second block member 114 by pulling upward on the secured wire member 44.

The wire station 110 in FIG. 6, although not illustrated as having a weighted bag disposed upon the bottom of the base platform 42, may include a weighted bag as discussed in detail above. Thus, the device can be utilized connected to the manifold or remote from the manifold. Similarly, although the wire station in FIG. 6 is not illustrated as having shielding devices to aid in separation and control of the wire members 44 and 46 disposed thereon, these devices may easily be incorporated into the final wire station design.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is of course defined in the language in which the appended claims are expressed.

What is claimed is:

1. A medical device comprising:
   a first wire;
   a second wire;
   a catheter, the catheter defining at least one wire lumen for passage of the first wire therethrough, and the second wire therethrough, the catheter having a proximal end region and a distal end region, the proximal end region comprising a manifold,
      the manifold defining at least one port, the at least one port being in communication with the at least one wire lumen;
   a wire station system, the wire station system comprising a base platform and a manifold engagement mechanism, the manifold engagement mechanism constructed and arranged to removably engage the base platform to an engagement region of the manifold, the base platform having a wire management system,
      the wire management system being actuatable between a first and a second position, in the first position each wire being moveable along a longitudinal axis, in the second position at least one of the wires being fixedly engaged to the wire management system.

2. The medical device of claim 1 wherein the catheter is a bifurcated catheter.

3. The medical device of claim 1 wherein the catheter defines a first wire lumen and a second wire lumen separate from the first wire lumen.

4. The medical device of claim 3 wherein the manifold comprises a plurality of ports, at least one of the ports being in communication with the first wire lumen and the second wire lumen.

5. The medical device of claim 1 wherein the wire management system comprises a first wire securement mechanism and a second wire securement mechanism, each securement mechanism being independently actuatable between the first position and the second position.

6. The medical device of claim 5 wherein each securement mechanism is a clothespin-type securement mechanism.

7. The medical device of claim 5 wherein each securement mechanism is a cullet-type securement mechanism.

8. The medical device of claim 5 wherein each securement mechanism is a magnetic wire securement mechanism.

9. The medical device of claim 5 wherein each securement mechanism is a cam-type wire securement mechanism.

10. The medical device of claim 5 wherein each securement mechanism is a partial slit wire securement mechanism.

11. The medical device of claim 1 wherein at least one of the first wire and second wire is a guidewire.

12. A medical device comprising:
   a catheter, the catheter defining at least one wire lumen for passage of a first wire therethrough, and a second wire therethrough, the catheter having a proximal end region and a distal end region, the proximal end region comprising a manifold, the manifold defining at least one port, the at least one port being in communication with the at least one wire lumen;

a wire station system, the wire station system comprising a base platform and a manifold engagement mechanism, the manifold engagement mechanism constructed and arranged to removably engage the base platform to an engagement region of the manifold, the base platform having a wire management system configured to engage and selectively fix the first wire and the second wire relative to the base platform, wherein the wire management system is actuatable between a first and a second position, in the first position each wire being moveable relative to the base platform and, in the second position, each wire being fixed relative to the base platform.

13. The medical device of claim 12 wherein the catheter is a bifurcated catheter.

14. The medical device of claim 12 wherein the wire management system comprises a first wire securement mechanism and a second wire securement mechanism, each securement mechanism being independently actuatable between the first position and the second position.

15. The medical device of claim 14 wherein each securement mechanism is a clothespin-type securement mechanism.

16. The medical device of claim 14 wherein each securement mechanism is a cullet-type securement mechanism.

17. The medical device of claim 14 wherein each securement mechanism is a magnetic wire securement mechanism.

18. The medical device of claim 14 wherein each securement mechanism is a cam-type wire securement mechanism.

19. The medical device of claim 14 wherein each securement mechanism is a partial slit wire securement mechanism.

20. The medical device of claim 12 wherein at least one of the first wire and second wire is a guidewire.

* * * * *